United States Patent
Matos et al.

(10) Patent No.: US 6,610,894 B2
(45) Date of Patent: Aug. 26, 2003

(54) INCREASING ENANTIOSELECTIVITY IN REDUCTIONS WITH BORANE REAGENTS

(75) Inventors: Karl Matos, Pittsburgh; Joseph A. Corella, II, Wexford; Elizabeth R. Burkhardt, Bridgeville; Shawn M. Nettles, Mars, all of PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 176 days.

(21) Appl. No.: 09/771,230

(22) Filed: Jan. 26, 2001

(65) Prior Publication Data

US 2001/0047116 A1 Nov. 29, 2001

Related U.S. Application Data

(63) Continuation of application No. 09/553,264, filed on Apr. 20, 2000, now Pat. No. 6,218,585.

(51) Int. Cl.$^7$ .............................................. C07C 27/00
(52) U.S. Cl. ...................................... 568/814; 568/881
(58) Field of Search .................................. 568/814, 881

(56) References Cited

U.S. PATENT DOCUMENTS 4,943,635 A * 7/1990 Corey ........................... 546/13
6,218,585 B1 * 2/2001 Matos ......................... 568/814

* cited by examiner

Primary Examiner—Samuel Barts
(74) Attorney, Agent, or Firm—J. G. Uber; H. E. Bartony, Jr.

(57) ABSTRACT

A method of increasing enantioselectivity in a reduction reaction of a prochiral substrate with a borane reagent including a borohydride species (for example, a borohydride stabilized borane-tetrahydrofuran complex) catalyzed by a chiral catalyst includes the step of maintaining the concentration of borohydride species in the borane reagent below approximately 0.005 M during the reduction of the prochiral substrate. A method of increasing enantioselectivity in a reduction reaction of a prochiral substrate with a borane reagent including a borohydride species that is catalyzed by a chiral catalyst includes the step of reducing the detrimental effect the borohydride species has on enantioselectivity by adding a Lewis acid. For example, the prochiral substrate can be a ketone and the chiral catalyst can be a chiral oxazaborolidine.

9 Claims, 3 Drawing Sheets

INCREASING ENANTIOSELECTIVITY IN REDUCTIONS WITH BORANE REAGENTS

This application is a continuation of Ser. No. 09/553,264 filed Apr. 20, 2000 now U.S. Pat. No. 6,218,585.

FIELD OF THE INVENTION

The present invention relates to increasing enantioselectivity in reactions with borane reagents, and especially, to increasing enantioselectivity in the reduction of a prochiral substrate with a borane reagent and a chiral catalyst.

BACKGROUND OF THE INVENTION

Borane reagents such as borane-tetrahydrofuran complex (sometimes referred to as THFB) are valuable reagents for the reduction of functional groups and for hydroboration reactions with carbon-carbon double and triple bonds. For example, functional groups reduced by borane-tetrahydrofuran complex include aldehyde, ketone, acyl chloride, lactone, epoxide, ester, amide, oxime, imine, and nitrile. Borane-tetrahydrofuran complex is a very selective and clean reducing agent. Because the borane is complexed to the low-boiling (65° C.), common solvent, tetrahydrofuran, no byproduct residues are generated. Typically a reduction is quenched with excess methanol to deactivate any remaining borane-tetrahydrofuran complex and distilled to remove the boron from the desired products as the methylborate/methanol azeotrope.

The enantioselective reduction of prochiral ketones with borane-tetrahydrofuran complex in the presence of an oxazaborolidine chiral catalyst such as (R)-MeCBS (a methyl-substituted chiral oxazaborolidine named after Corey, Bakshi, and Shibata) is a very important tool for the synthesis of alcohols in high optical purity. See, for example, Corey, E. J. and Helel, C. J., "Reduction of Carbonyl Compounds with Chiral Oxazaborolidine Catalysts: A New Paradigm for Enantioselective Catalysis and a Powerful New Synthetic Method," *Angew. Chem. Int. Ed.*, 37, 1986–2012 (1998); U.S. Pat. No. 4,943,635; and Franot, C. et al., A Polymer-Bound Oxazaborolidine Catalysts: "Enantioselective Borane Reductions of Ketones," *Tetrahedron: Asymmetry*, 6:11, 2755–2766 (1995).

However, the selectivity of the reaction has been found to be affected by a number of parameters including, for example, temperature and borane source/batch. In that regard, the enantioselectivity of (R)-MeCBS catalyzed reductions has been found to be quite low for various commercial samples of THFB. Several researchers have presumed that the widely variable results achieved with commercially available THFB were a result of decomposition thereof. See Jones, T. K. et al., "An Asymmetric Synthesis of MK-0417. Observations on Oxazaborolidine-Catalyzed Reductions," *J. Org. Chem.*, 56, 763–769 (1991).

In that regard, although THFB is a very valuable reagent, THFB complexes are known to decompose during transportation and storage at ambient temperature and to thermally decompose during reaction. To prevent decomposition during transportation and storage, stabilizers are typically added to borane-tetrahydrofuran complex. Typically, a hydride source such as a metal hydride (for example, potassium hydride, sodium hydride or lithium hydride) or sodium borohydride ($NaBH_4$) is added to THFB. Sodium borohydride and other hydrides have been shown to be quite effective in stabilizing THFB. At least one study has also shown that sodium borohydride leads to strongly enhanced activity in the reduction of ketones. Jockel, H. and Schmidt, R., "Kinetics of Direct Borane Reduction of Pinacolone in THF," *J. Chem. Soc.*, Perkin Trans. 2, 2719–2723 (1997). Other borohydride sources include, for example, potassium borohydride, lithium borohydride, and tetraalkylammonium borohydride. Moreover, metal alkoxides (for example, sodium tert-butoxide, potassium tert-butoxide, lithium tert-butoxide, sodium tert-amylate, potassium tert-amylate, lithium tert-amylate, sodium isopropoxide, potassium isopropoxide, lithium isopropoxide, sodium methoxide, potassium methoxide and lithium methoxide) can be added to generate a borohydride stabilizing agent within THFB.

It is very desirable to develop borane compositions and methods of reaction that improve enantioselectivity.

SUMMARY OF THE INVENTION

In one aspect, the present invention provides a method of increasing enantioselectivity in a reduction reaction of a prochiral substrate with a borane reagent including or containing a borohydride species (for example, a borohydride stabilized borane-tetrahydrofuran complex) catalyzed by a chiral catalyst. As used herein, the term "borohydride species" refers to compounds of boron and hydrogen and includes, for example, anionic borohydrides. The method includes generally the step of limiting the concentration of borohydride species in the borane reagent (for example, borane-tetrahydrofuran complex). In the case of borane-tetrahydrofuran complex, the method includes generally the step of maintaining the concentration of borohydride species in the borane-tetrahydrofuran complex below approximately 0.005 moles per mole of $BH_3$ during the reduction of the prochiral substrate. More preferably, the concentration of borohydride species in the borane-tetrahydrofuran complex is below approximately 0.0015 moles per mole of $BH_3$ during the reduction of the prochiral substrate. Most preferably, the concentration of borohydride speicies in the borane-tetrahydrofuran complex is below approximately 0.0005 moles per mole of $BH_3$ during the reduction of the prochiral substrate. Prochiral substrates suitable for use in the present invention include, for example, ketones, imines and oximes.

As used herein and as used commonly in the chemical arts, the term "ketone" refers generally to a compound having the formula:

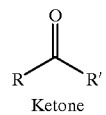
Ketone

The term "imine" refers generally to a compound having the formula:

The term "oxime" refers generally to a compound having the formula:

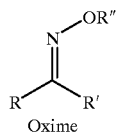
Oxime

In the above formulas, R and R' are preferably independently different, an alkyl group or an aryl group (Ar). R" is preferably H, —SiR$_3$ or an alkyl group. Reductions of such prochiral substrates are discussed, for example, in Tilyer, R. D. et al., "Asymmetric Reduction of Keto Oxime Ethers Using Oxazaborolidine Reagents. The Enantioselective Synthesis of Cyclic Amino Alcohols," *Tetrahedron Letters,* 36:25, 4337–4440 (1995); Cho, B. T. and Ryu, M. H., "Asymmetric Borane Reduction of Ketoxime O-Trimethylsilyl Ethers Mediated by a Chiral 1,3,2-Oxazaborolidine Derived from (−)-Ephedrine," *Bull. Korean Chem. Soc.,* 15:3, 191–192 (1994); and Shimizu, M. et al., "Stereocontrol in the Reduction of 1,2-Diimine with an Oxazaborolidine Catalyst. Highly Stereoselective Preparation of (R,R)-1,2-Diphenyl-ethylenediamine," *Tetrahedron Letters,* 36:47, 8607–8610 (1995).

Borane-tetrahydrofuran complex and other borane reagents may be prepared in a manner to maintain the concentration of borohydride species in the borane-tetrahydrofuran complex below a desired level (for example, below approximately 0.005 moles per mole of BH$_3$ in the case of borane-tetrahydrofuran complex. For example, borane-tetrahydrofuran complex may be prepared by the addition of diborane to tetrahydrofuran with a known amount of a borohydride stabilizer. In that regard, a known amount of a borohydride stabilizer can be added. As used herein, the term "borohydride stabilizer" refers generally to borohydride compounds such as sodium borohydride and to compound(s) that generate a borohydride species within the borane-tetrahydrofuran complex. Alternatively, borane-tetrahydrofuran complex can be made without using a borohydride stabilizer. Preferably, borane-tetrahydrofuran complex is stored at or below 20° C. before the reduction reaction to reduce decomposition.

Borane-tetrahydrofuran complex and other borane reagents may also be prepared with a concentration of borohydride species greater than a desired threshold concentration (for example 0.005 moles per mole of BH$_3$ in the case of borane-tetrahydrofuran complex), and the concentration of borohydride species decreased before the reduction reaction. The concentration of borohydride species may, for example, be decreased by the addition of a Lewis acid. Example of a suitable Lewis acid include BF$_3$, BF$_3$ etherate complex (for example, BH$_3$—THF), ZrCl$_4$, AlCl$_3$, FeCl$_3$ or TiCl$_4$.

In the case of borane-tetrahydrofuran complex, the concentration of borane-tetrahydrofuran complex per liter of tetrahydrofuran is preferably at least 1.0M. More preferably, the concentration of borane-tetrahydrofuran complex per liter of tetrahydrofuran is at least 1.5M. Most preferably, the concentration of borane-tetrahydrofuran complex per liter of tetrahydrofuran is at least 2.0M.

Preferably, the prochiral substrate is added to a mixture of borane reagent (for example, borane-tetrahydrofuran complex) and chiral catalyst. The case that the prochiral substrate is a ketone and the chiral catalyst is a chiral oxazaborolidine is an example of a reduction reaction of the present method.

In another aspect, the present invention provides a method of increasing enantioselectivity in a reduction reaction of a prochiral substrate with a borane reagent including a borohydride species that is catalyzed by a chiral catalyst. The method includes the step of reducing the detrimental effect the borohydride species has on enantioselectivity by adding a Lewis acid. Borane reagents suitable for use in the present invention include, but are not limited to, borohydride stabilized borane-tetrahydrofuran complex, as well as dimethylsulfide borane (DMSB) or diethylanilineborane (DEANB) when, for example, prepared from sodium borohydride. As discussed above, suitable Lewis acids include, but are not limited to, BF$_3$, BF$_3$ etherate complex, ZrCl$_4$, AlCl$_3$, FeCl$_3$ or TiCl$_4$. Preferably, the Lewis acid is BF$_3$ or BF$_3$ etherate complex.

In the case that a borohydride stabilized borane-tetrahydrofuran complex is used, the concentration of borane-tetrahydrofuran complex per liter of tetrahydrofuran is preferably at least 1.0M. More preferably, the concentration of borane-tetrahydrofuran complex per liter of tetrahydrofuran is at least 1.5M. Most preferably, the concentration of borane-tetrahydrofuran complex per liter of tetrahydrofuran is at least 2.0M. The borane-tetrahydrofuran complex is preferably stored at a temperature at or below approximately 20° C. prior to reaction. Likewise, the prochiral substrate is preferably added to a mixture of borane-tetrahydrofuran complex and chiral catalyst.

DETAILED DESCRIPTION OF THE INVENTION

Figure 1:
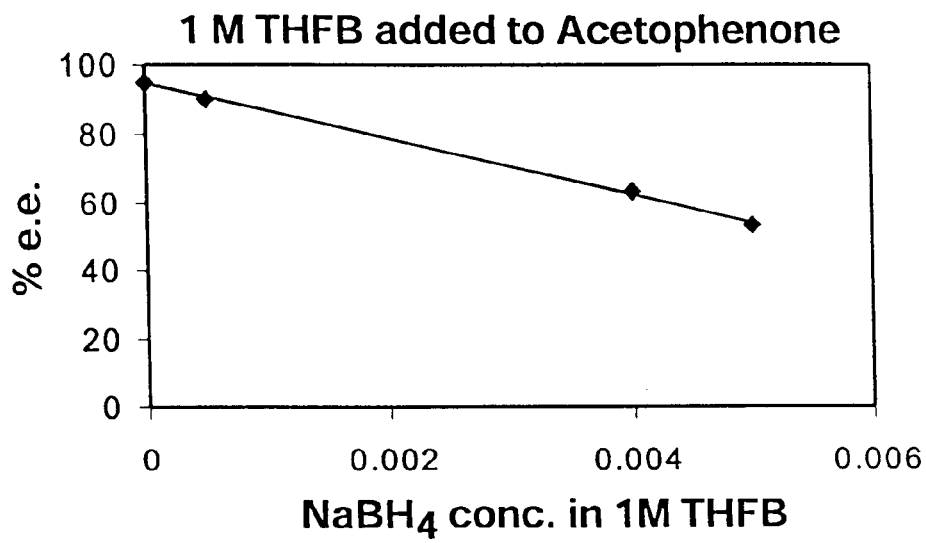
FIG. 1 illustrates the effect of sodium borohydride concentration on percent enantiomeric excess (% ee) in the reduction of acetophenone with THFB.

It is believed that borohydride species, when added to or generated within a borane reagent, are detrimental to the enantioselectivity of an enantioselective or chiral catalytic reduction (using, for example a chiral catalyst such as (R)-MeCBS catalyst) of prochiral compounds/substrates such as ketones. In a number of studies, borohydride stabilizing agents such as sodium borohydride (or a borohydride decomposition product or products thereof) were shown to have a negative effect on enantioselectivity of chiral catalyzed reductions with THFB. Enantioselectivity was greatly improved in model reactions with THFB having reduced concentrations of borohydride species or no borohydride as compared to similar reaction with THFB having greater concentrations of borohydride.

For example, even quite small concentrations of the borohydride stabilizer sodium borohydride in 1.0M THFB resulted in reduced enantioselectivity. Kinetic experiments showed THFB samples with sodium borohydride stabilizer reduced prochiral substrates such as ketones (in a racemic fashion) faster than non-stabilized THFB. As a result of the competitive reaction, the addition of the prochiral substrate (for example, a ketone) to the THFB/catalyst mixture is a preferred mode of addition in a chiral catalyzed reduction. Moreover, it was surprisingly discovered that increasing the concentration of borane in THFB complexes increases enantioselectivity in the reduction of prochiral substrates such as ketones.

The present invention was demonstrated with several studies of (R)-MeCBS catalyzed reductions of ketones with THFB.

Reduction of Ketones with Stabilized and Non-stabilized THFB Solutions

Several studies of (R)-MeCBS catalyzed asymmetric reductions of ketones (shown generally in equation (1) below) focused on the enantioselectivity of THFB containing sodium borohydride stabilizer. The reduction of acetophenone with a commercially available 1M THFB (Callery Chemical of Callery, Pa.) containing sodium borohydride gave a surprisingly low enantioselectivity of phenethyl alcohol product (46.6 % ee). In comparison, using DMSB or DEANB as borane sources prepared from diborane, enantioselectivities of >95% were observed. Similar low enantioselectivities were obtained when THFB with sodium borohydride was utilized in the (R)-MeCBS reduction of other ketones (see Table I). In the studies of Table I, a solution of 1M THFB was also prepared without any $NaBH_4$ stabilizer, and that solution was used in reductions on the same series of ketones as reduced with the commercially available THFB with stabilizer. The mode of addition was THFB added to ketone/(R)-MeCBS in all experiments of Table I.

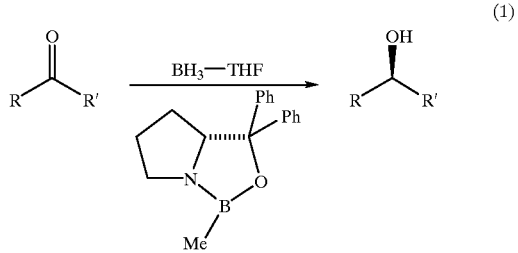

(1)

TABLE I

| | | % ee obtained | |
|---|---|---|---|
| Exp. # | ketone | THFB commercial | THFB without $NaBH_4$ |
| 1-1 | acetophenone | 46.6% | 95.2% |
| 1-2 | 3-methyl-2-butanone | 32.8% | 61.0% |
| 1-3 | cyclohexylmethyl ketone | 37.4% | 60.6% |
| 1-4 | α-tetralone | 66.4 | 84.8% |
| 1-5 | 3,3-dimethylbutanone | 45.8 | 90.6 |

In contrast to the low enantioselectivities achieved when the reduction was carried out with borohydride stabilized THFB, high enantioselectivities were obtained when non-stabilized THFB solutions (that is, THFB solutions without sodium borohydride or other borohydride species therein) were used as the reducing agent (see Table I). In experiment 1—1 of Table I (reduction of acetophenone), for example, a dramatic increase in enantioselectivity from 46.6 to 95.2 % ee was observed.

Selectivity Enhancement of Borane Reagents Including Borohydride Species

From these and other experiments, it was evident that borohydride species such as those that result from addition of sodium borohydride stabilizer to THFB have a negative effect on the enantioselectivity of reductions with chiral catalysts such as (R)-MeCBS. Two solutions were envisioned to increase the enantioselectivity in reductions with borane reagents:

1. Limiting or eliminating the amount of borohydride species in the borane reagent; and
2. Adding a compound (for example, boron trifluoride $BF_3$) to reduce or eliminate the negative effect of the borohydride species.

A. Limiting or Eliminating Borohydride Stabilizers

1. Borohydride Concentration

Several experiments were performed to study the effect of decreasing the amount of borohydride stabilizer in THFB solutions to increase enantioselectivity. In the studies of Table II and Table III, for example, 1.0M THFB solutions containing different amounts of sodium borohydride were prepared to determine if a minimal concentration of sodium borohydride could be utilized while still achieving good enantioselectivity in the (R)-MeCBS reduction. Reductions of the substrates (acetophenone and pinacolone) were carried out with these solutions and the percent enantiomeric excess of the products was measured via chiral gas chromotography. A generally linear, inverse relationship between the amount of the model $NaBH_4$ stabilizer present in the THFB and the percent enantiomeric excess of product was found (see FIGS. 1 and 2). In other words, the less $NaBH_4$ present in the THFB, the higher the percent enantiomeric excess of the product alcohol.

TABLE II

| Exp. # | ketone | $NaBH_4$ conc. in 1 M THFB | % ee |
|---|---|---|---|
| 2-1 | acetophenone | 0.005 | 53.2 |
| 2-2 | acetophenone | 0.004 | 63.2 |
| 2-3 | acetophenone | 0.0005 | 90.4 |
| 2-4 | acetophenone | No stabilizer | 95.2 |

Figure 2:
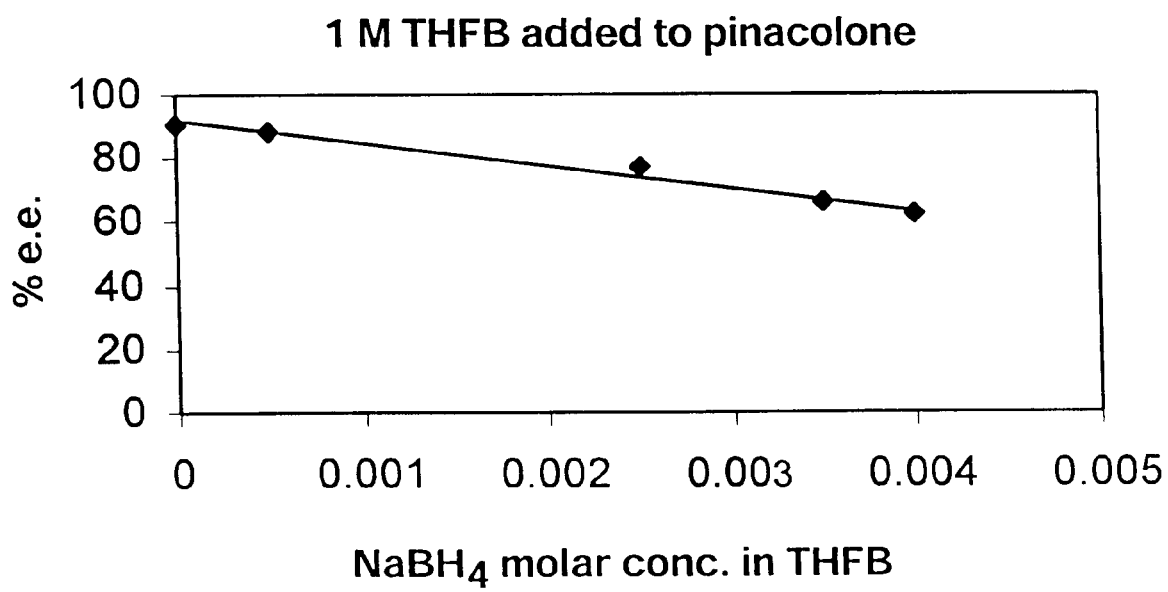
FIG. 2 illustrates the effect of sodium borohydride concentration on enantioselectivity in the reduction of pinacolone with THFB.

A plot of selectivity versus concentration of $NaBH_4$ in THFB in FIG. 1 showed that even at a concentration of approximately 0.0005M of sodium borohydride the enantioselectivity in the reduction of acetophenone was less than observed in the absence of sodium borohydride. This study clearly indicates that even relatively low concentrations of sodium borohydride in THFB solutions significantly affect the selectivity of the reduction.

TABLE III

| Exp. # | ketone | NaBH$_4$ conc. in 1 M THFB | % ee |
|---|---|---|---|
| 3-1 | pinacolone | 0.004 M | 62.2 |
| 3-2 | pinacolone | 0.0035 M | 66.2 |
| 3-3 | pinacolone | 0.0025 M | 77.2 |
| 3-4 | pinacolone | 0.0005 M | 88 |
| 3-5 | pinacolone | no stabilizer | 90.6 |

The amount of sodium borohydride used to prepare the various solutions was added to the THFB preparation. $^{11}$B NMR studies of those solutions indicated the sodium borohydride was converted to $B_3H_8^-$. It is believed that anionic borohydride species are responsible for the lower enantioselectivities observed with borohydride stabilized THFB.

2. Mode of Addition

Figure 3:
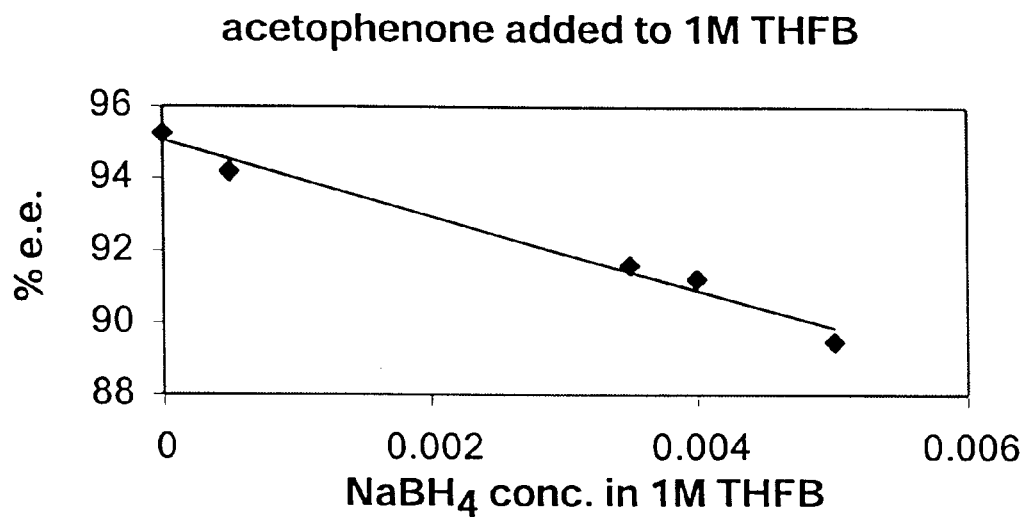
FIG. 3 illustrates a study of the effect of sodium borohydride concentration on enantioselectivity in the case of addition of acetophenone to a mixture of THFB and (R)-MeCBS.

A parameter further investigated to improve the enantioselectivity of reduction reactions with THFB and CBS catalysts was the mode of addition of THFB. Higher enantioselectivities in such reductions were obtained when the ketone (for example, acetophenone or pinacolone) was added to a mixture of a commercially available THFB (including sodium borohydride stabilizer) and MeCBS catalyst. Even better enantioselectivities were observed using THFB solutions with reduced concentrations of sodium borohydride when the ketone was added to the THFB/sodium borohydride/MeCBS mixture (see Tables IV and V). In the case of acetophenone, for example, when the concentration of sodium borohydride in THFB was lower than 0.0035M (see Table IV and FIG. 3), the enantioselectivity was greater than 91.6 when the ketone was added to the THFB/sodium borohydride/Me-CBS mixture.

TABLE IV

| Exp. # | ketone | NaBH$_4$ conc. in 1 M THFB (M) | % ee |
|---|---|---|---|
| 4-1 | acetophenone | 0.005 | 89.5 |
| 4-2 | acetophenone | 0.004 | 91.2 |
| 4-3 | acetophenone | 0.0035 | 91.6 |
| 4-4 | acetophenone | 0.0005 | 94.2 |
| 4-5 | acetophenone | no stabilizer | 95.2 |

TABLE V

| Exp. # | ketone | NaBH$_4$ conc. in 1 M THFB | % ee |
|---|---|---|---|
| 5-1 | pinacolone | 0.004 M | 82.6 |
| 5-2 | pinacolone | 0.0025 M | 87 |
| 5-3 | pinacolone | 0.0005 M | 93 |
| 5-4 | pinacolone | no stabilizer | 94.8 |

Figure 4:
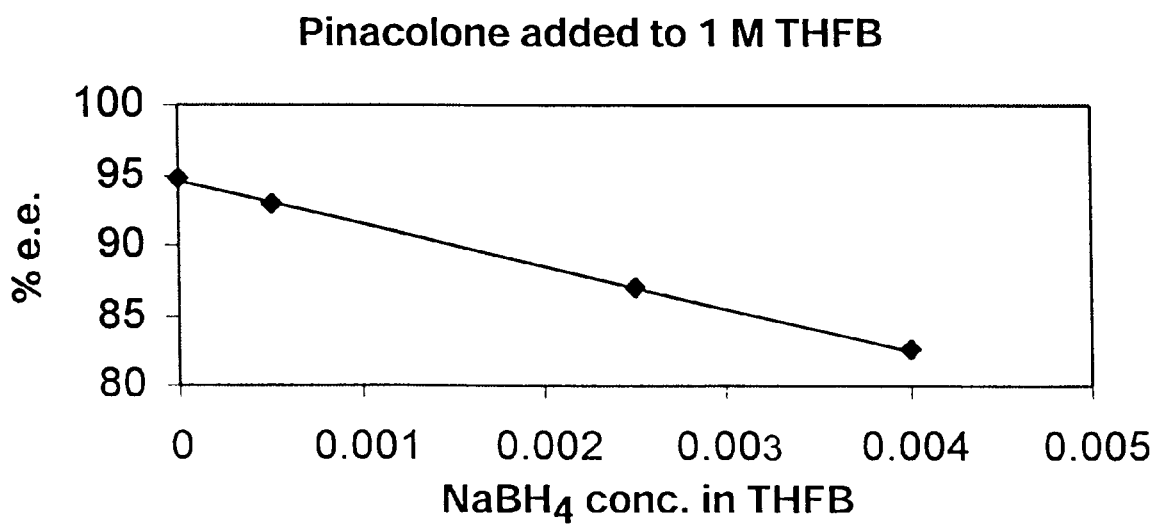
FIG. 4 illustrates the effect of sodium borohydride concentration on enantioselectivity in the case of addition of pinacolone to a mixture of THFB and (R)-MeCBS.

In the experiments of Tables IV and V (displayed graphically in FIGS. 3 and 4, respectively), acetophenone and pinacolone were reduced using 1M THFB. The THFB/(R)-MeCBS solution was stirred for approximately 10 minutes before addition of the ketone, allowing for equilibration. Experiments were performed using THFB solutions with different concentrations of NaBH$_4$ stabilizer. Once again, these experiments showed a higher percent enantiomeric excess of the product alcohol than the same reductions performed adding THFB to ketone/(R)-MeCBS.

3. Kinetic Experiments

The dramatic differences in enantioselectivities observed between sodium borohydride stabilized THFB and non-stabilized THFB solutions prompted several kinetic experiments. To determine the relative reactivity of borane towards a ketone (acetophenone) by: (1) sodium borohydride stabilized THFB, (2) non-stabilized THFB, and (3) non-stabilized THFB with MeCBS, three experiments were carried out.

Figure 5:
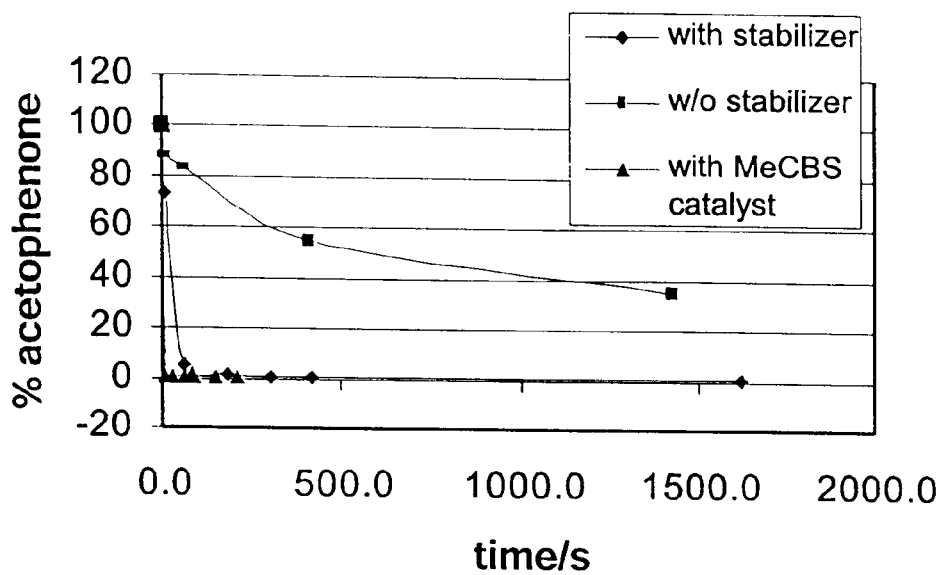
FIG. 5 illustrates a study of the reduction of a ketone (acetophenone) with THFB including sodium borohydride stabilizer, with THFB without sodium borohydride stabilizer, and with THFB and (R)-MeCBS catalyst.

Each experiment was started at 0° C. by rapid introduction of THFB into the ketone. A slight exotherm (approximately 6° C.) was observed when the non-stabilized THFB was added to the ketone/THF mixture. However, a very large exotherm was observed when commercial, sodium borohydride stabilized THFB or THFB/MeCBS catalyst was used. The exotherm observed with commercial, borohydride stabilized THFB indicates that borohydride stabilized THFB reduces acetophenone faster than non-stabilized THFB (see FIG. 5). In FIG. 5, a plot of %acetophenone disappearance versus time for the three experiments discussed above showed that the fastest reaction occurred when MeCBS was used as the catalyst. Without MeCBS catalyst and sodium borohydride stabilizer, the reduction is quite slow. However, when sodium borohydride is present with an enantioselective catalyst such as MeCBS, the non-selective reduction competes with the MeCBS catalyzed reaction. Even though the reduction reaction of the ketone catalyzed by (R)-MeCBS is faster than the non-chiral reaction promoted or catalyzed by the borohydride species, the non-chiral pathway promoted or catalyzed by borohydride species lowers the overall selectivity of the (R)-MeCBS reduction.

4. Concentration of THFB Complex

The effect on enantioselectivity of using more concentrated THFB solutions was also studied. Surprisingly, when adding borane solution to the ketone, the enantioselectivity of the MeCBS reduction of acetophenone with a commercially available, sodium borohydride stabilized 2.0M solution of THFB (having a NaBH$_4$ concentration of 0.008 M) was superior to the reduction with a commercially available, sodium borohydride stabilized 1.0M solution of THFB (having a NaBH$_4$ concentration of 0.005 M) using the same mode of addition (for example, 79.6 % ee vs. 45.6 % ee as determined by chiral gas chromotography). (See Table VI and FIG. 6). The mechanism of the effect of THFB concentration on enantioselectivity is not completely understood. In the experiments of Table VI, the mode of addition was THFB to ketone/(R)-MeCBS.

TABLE VI

| Exp. # | ketone | NaBH$_4$ conc. in 2.0 M THFB | % ee |
|---|---|---|---|
| 6-1 | acetophenone | 0.008 | 79.6 |
| 6-2 | acetophenone | 0.005 | 85.6 |
| 6-3 | acetophenone | 0.0035 | 90.4 |
| 6-4 | acetophenone | 0.0015 | 91.2 |
| 6-5 | acetophenone | No stabilizer | 93.8 |

Figure 6:
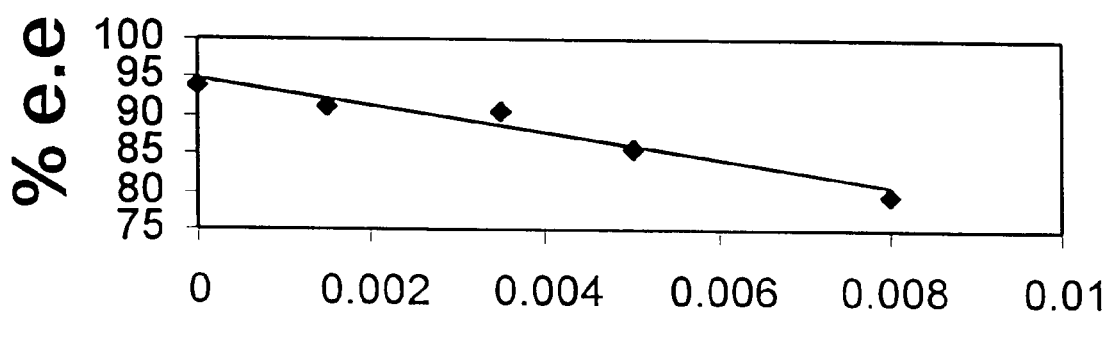
FIG. 6 illustrates a study of the effect of THFB concentration on enantioselectivity at various concentration of sodium borohydride stabilizer.

Enantioselectivity improved with 2.0M THFB solutions as the concentration of sodium borohydride stabilizer was reduced (see FIG. 6). This trend is similar to the results obtained with 1.0M THFB solutions. These results again demonstrate the detrimental effect of borohydride stabilizer in the MeCBS reduction of ketones.

In U.S. patent application Ser. No. 09/218,914, assigned to the assignee of the present invention, the disclosure of which is incorporated hereing by reference, it is disclosed that THFB can be stabilized for extended periods of time by reducing the temperature of the THFB. In that regard, the temperature of the THFB complex is preferably maintained at or below 20° C. More preferably, the temperature is maintained in the range of approximately −40° C. to 20° C. Most preferably, the temperature is maintained in the range of approximately −20° C. to 5° C. By reducing the temperature of the THFB complex, even relatively high concentration (for example, concentration of 2.0 M and above) of THFB complex per liter of tetrahydrofuran can be stabilized for extended periods of time at low concentration of borohydride stabilizer or without the presence of a stabilizer. Thus, in one aspect of the present invention, enantioselectivity can be increased by storing relatively highly concentrated THFB without borohydride stabilizer or with very low concentrations of borohydride stabilizer at reduced temperature for a subsequent MeCBS catalyzed reduction of a ketone. Preferably, THFB for use in the present invention is prepared by the direct route of addition of diborane to THF rather than from sodium borohydride to precisely control or eliminate the concentration of sodium borohydride in the product.

B. Elimination of Borohydride Stabilizer Present in THFB

1. Addition of Lewis Acids

As discussed above, enantioselectivity can be improved in THFB stabilized with a borohydride species by adding one or more compounds that reduce the adverse effect of the borohydride by, for example, reducing the concentration of borohydride or by preventing the borohydride from promoting or catalyzing a racemic reduction. One or more compounds such as Lewis acids can, for example, be added to THFB stabilized with borohydride to react with the borohydride and convert it to a chemical species that does not significantly adversely affect enantioselectivity.

Other borane sources/reagents containing borohydride species/components will also give lower enantioselectivities in the reduction of prochiral compounds with oxazaborolidine or other chiral catalysts. For example, dimethylsulfide borane or diethylaniline borane when prepared from sodium borohydride may contain borohydride species as impurities. To achieve a high degree of enantioselectivity in a chiral reduction with these borane sources or borane reagents, preparation methods for the boranes preferably minimize or eliminate the formation of borohydride impurities. For example, dimethylsulfide borane and diethylaniline borane when prepared from diborane and the respective Lewis base contain no borohydride components. Moreover, the addition of a Lewis acid to a borane reagent containing a borohydride species or to a catalyst reaction mixture thereof will restore the enantioselectivity of the reaction.

In several studies, the addition of a Lewis acid (approximately 3–5% of $BF_3$—THF complex) to the acetophenone/(R)-MeCBS solution prior to the THFB loading was investigated to remove the stabilizer from THFB. Lewis acids including, but not limited to, $BF_3$—THF complex, $ZrCl_4$, $AlCl_3$, $FeCl_3$ and $TiCl_4$, act to convert sodium borohydride to THFB. To be an effective additive in the reaction, the reaction of a compound such as $BF_3$—THF with the stabilizer is preferably a faster reaction than the ketone reduction with the THFB/$NaBH_4$ mixture. A $^{11}B$ NMR study in which $BF_3$—THF was reacted with a THFB solution stabilized with a known amount of sodium borohydride, showed that the reaction of $BF_3$—THF with sodium borohydride is indeed a very fast reaction to produce THFB. Thus, the treatment of MeCBS/ketone mixture with $BF_3$—THF resulted in a highly selective reduction of acetophenone (92.8 % ee). By utilizing $BF_3$—THF as an additive in the reaction, a similar selectivity to non-stabilized THFB (95 % ee) can be obtained. The ability to add a compound to a THFB solution that has been stabilized with sodium borohydride to decrease or eliminate the negative effect of sodium borohydride enables one to first stabilize a THFB solution with sodium borohydride for storage without significant decomposition and then to treat the THFB with the compound to substantially restore the enantioselectivity of the reduction. Once again, the stabilized THFB can be stored at relatively low temperatures as described above to reduce the amount of borohydride stabilizer needed to prevent substantial decomposition.

Table VII summarizes several studies using commercially available 1M THFB (Callery Chemical) with 5 mol % $BF_3$—THF added to reduce the concentration of or eliminate the $NaBH_4$ stabilizer present in the THFB reagent.

TABLE VII

| Exp. # | ketone | % ee. | Mode of Addition |
| --- | --- | --- | --- |
| 7-1 | acetophenone | 92.8 | THFB added to ketone/(R) -MeCBS/ $BF_3$-THF |
| 7-2 | acetophenone | 90.4 | THFB/$BF_3$-THF added to ketone/ (R)-MeCBS |
| 7-3 | acetophenone | 86.4 | Ketone added to THFB/$BF_3$-THF/ (R)-MeCBS |

Table VIII summarizes several studies of a reduction performed using a commercially available 2M THFB (Callery Chemical) with 5 mol % $BF_3$—THF added to reduce the concentration of or eliminate the $NaBH_4$ stabilizer present in the THFB reagent.

TABLE VIII

| Exp. # | ketone | % ee | Mode of Addition |
| --- | --- | --- | --- |
| 8-1 | acetophenone | 90.2 | THFB added to ketone/(R) - MeCBS/ $BF_3$-THF |
| 8-2 | acetophenone | 86.8 | THFB/$BF_3$-THF added to ketone/(R)-MeCBS |
| 8-3 | acetophenone | 90.6 | Ketone added to THFB/$BF_3$-THF/(R)-MeCBS |

The data of Tables VII and Table VIII demonstrate that enantioselectivity is enhanced by addition of a Lewis acid such as $BF_3$ regardless of the manner/timing in which the $BF_3$ is incorporated.

Table IX illustrates the results of several experiments in which Lewis acids other than $BF_3$ were added to a reaction mixture including borohydride stabilized THFB. Once again, enantioselectivity was enhanced by addition of the Lewis acid.

TABLE IX

| Exp. # | Lewis acid | % e.e. | Mode of Addition |
| --- | --- | --- | --- |
| 9-1 | $ZrCl_4$ | 85.6 | THFB/$ZrCl_4$ added to acetophenone/(R)-MeCBS |
| 9-2 | $AlCl_3$ | 83.0 | THFB/$AlCl_3$ added to acetophenone/(R)-MeCBS |

TABLE IX-continued

| Exp. # | Lewis acid | % e.e. | Mode of Addition |
|---|---|---|---|
| 9-3 | $FeCl_3$ | 86.0 | THFB/$FeCl_3$ added to acetophenone/(R)-MeCBS |
| 9-4 | $TiCl_4$ | 82.6 | THFB $TiCl_4$ added to acetophenone/(R)-MeCBS |

2. Studies of the Effect of $NaBF_4$

Reductions were also performed using 1M THFB without $NaBH_4$ added stabilizer but with added 5 mol % $NaBF_4$ to examine if the $NaBF_4$ (a byproduct of $NaBH_4$ and $BF_3$) has any influence on the reduction and the final percent enantiomeric excess of the chiral alcohol product. As indicated by the studies of Table X, the enantioselectivity of the chiral reduction using the $NaBF_4$ was nearly the same as experienced with commercial THFB with $BF_3$ additive. $NaBF_4$ has only a slightly negative effect on the enantioselectivity of the reaction. This result may explain why enantioselectivity in cases in which borohydride species are removed through the addition of a Lewis acid is slightly less than experienced in cases in which borane reagents are prepared in a manner to include no borohydride species.

TABLE X

| Exp. # | ketone | % ee | Mode of Addition |
|---|---|---|---|
| 9-1 | acetophenone | 92.8 | Ketone added to THFB/$NaBF_4$/(R)-MeCBS |
| 9-2 | acetophenone | 89.0 | THFB/$NaBF_4$ added to ketone/(R)-MeCBS |

3. Enantioselective Effect of $BF_3$—THF

Reductions were also performed adding 5 mol % $BF_3$—THF, using THFB without $NaBH_4$ stabilizer, to ensure that the $BF_3$—THF was not itself enhancing the selectivity of the reduction. The results of Table XI indicate that $BF_3$—THF complex does not itself substantially affect enantioselectivity and verify that borohydrides such as $NaBH_4$ inhibits the selectivity of the reduction. The $BF_3$—THF serves to "react out" the borohydride to yield a higher percent enantiomeric excess of product relative to the case of using a borane reagent such as THFB with a higher concentration of borohydride stabilizer present.

TABLE XI

| Exp. # | ketone | % ee | Mode of Addition |
|---|---|---|---|
| 10-1 | acetophenone | 91.8 | THFB/$BF_3$-THF added to ketone/(R)-MeCBS |
| 10-2 | acetophenone | 95.2 | Ketone added to THFB/$BF_3$-THF/(R)-MeCBS |

C. Borohydride Species

Several studies were made to identify the actual borohydride species influencing the enantioselectivity of the MeCBS reduction with THFB. Reductions were performed in which crude $NaB_3H_8$ (estimated at 0.7 mol % $NaB_3H_8$) was added to the reaction solution to examine its influence on the reduction. The $NaB_3H_8$ species present in commercially available THFB is formed from added stabilizer to prevent decomposition of the borane. The lowered enantioselectivity as illustrated in the studies of Table XII demonstrated that $NaB_3H_8$ acts as a non-selective catalyst in the ketone reduction.

TABLE XII

| Exp. # | ketone | % ee | Mode of Addition |
|---|---|---|---|
| 11-1 | acetophenone | 69.2 | THFB/$NaB_3H_8$ added to ketone/(R)-MeCBS |
| 11-2 | acetophenone | 88.6 | Ketone added to THFB/$NaB_3H_8$/(R)-MeCBS |

Experimental Procedure

EXAMPLE 1

Oxazaborolidine catalyzed reduction of acetophenone to 1-phenylethanol using borane-tetrahydrofuran (THFB) as the borane source.

A dry 100-mL three-necked, round-bottomed flask was charged with acetophenone (2 mL, 17.1 mmol) and dry THF (17 mL). The atmosphere was replaced with nitrogen. (R)-MeCBS in toluene (0.86 mL, 0.86 mmol) was then added, and the flask was placed in a water bath to moderate the temperature. Borane-tetrahydrofuran (10.3 mL, 10.3 mmol) was then slowly added to the reaction flask over an extended period of time. After completing addition of borane-tetrahydrofuran, the reaction solution was allowed to stir ten minutes before quench with 2M HCl (10 mL). Anhydrous diethyl ether (20 mL) was added, and the organic phase was washed with saturated aqueous solutions of KCl (3×8 mL), $NaHCO_3$ (3×12 mL) and KCl (3×8 mL). The organic layer was dried over $Na_2SO_4$, filtered, and analyzed by chiral GC for optical purity of the product alcohol, 1-phenylethanol.

EXAMPLE 2

Oxazaborolidine catalyzed reduction of acetophenone to 1-phenylethanol using borane-tetrahydrofuran (THFB) as the borane source. Mode of addition was ketone to the borane/catalyst solution.

A dry 100-mL three-necked, round-bottomed flask under nitrogen atmosphere was charged with borane-tetrahydrofuran (10.3 mL, 10.3 mmol) and (R)-MeCBS in toluene (0.86 mL, 0.86 mmol). The flask was then placed in a water bath to moderate the temperature. The borane solution was allowed to stir for 15 minutes. Acetophenone (2 mL, 17.1 mmol) in dry THF (17 mL) was then slowly added to the reaction flask over an extended period of time. After completing addition of borane-tetrahydrofuran, the reaction solution was allowed to stir ten minutes before quench with 2M HCl (10 mL). Anhydrous diethyl ether (20 mL) was added, and the organic phase was washed with saturated aqueous solutions of KCl (3×8 mL), $NaHCO_3$ (3×12 mL) and KCl (3×8 mL). The organic layer was dried over $Na_2SO_4$, filtered and analyzed by chiral GC for optical purity of the product alcohol, 1-phenylethanol.

EXAMPLE 3

Oxazaborolidine catalyzed reduction of acetophenone to 1-phenylethanol using borane-tetrahydrofuran (THFB)/5 mol % $BF_3$—THF.

A dry 100-mL three-necked, round-bottomed flask was charged with acetophenone (1.94 mL, 16.6 mmol) and dry THF (14.7 mL). The atmosphere was replaced with nitrogen. (R)-MeCBS in toluene (0.83 mL, 0.83 mmol) was then added, and the flask was placed in a water bath to moderate the temperature. Boron triflouride-tetrahydrofuran (0.09 mL, 0.81 mmol) was then added to the solution. Borane-tetrahydrofuran (10.0 mL, 10.0 mmol) was then slowly added to the reaction flask over an extended period of time. After completing addition of borane-tetrahydrofuran, the reaction solution was allowed to stir ten minutes before quench with 2M HCl (10 mL). Anhydrous diethyl ether (20 mL) was added and the organic phase was washed with saturated aqueous solutions of KCl (3×8 mL), $NaHCO_3$ (3×12 mL) and KCl (3×8 mL). The organic layer was dried over $Na_2SO_4$, filtered, and analyzed by chiral GC for optical purity of the product alcohol, 1-phenylethanol.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method of increasing enantioselectivity in a reduction reaction of a prochiral substrate with borane-tetrahydrofuran complex, the reduction reaction being catalyzed by a chiral catalyst, the method comprising the step of: adding the borane-tetrahydrofuran complex to a mixture of the prochiral substrate and the chiral catalyst, the concentration of the borane-tetrahydrofuran complex per liter of tetrahydrofuran being at least 1.0 M.

2. The method of claim 1 wherein the concentration of borane-tetrahydrofuran complex per liter of tetrahydrofuran is at least 1.5 M.

3. The method of claim 1 wherein the concentration of borane-tetrahydrofuran complex per liter of tetrahydrofuran is at least 2.0 M.

4. The method of claim 1 wherein the THFB complex is stored at a temperature at or below approximately 20° C. prior to reaction.

5. The method of claim 1 wherein the prochiral substrate is a ketone and the chiral catalyst is a chiral oxazaborolidine.

6. The method of claim 1 wherein the method further comprises the step of maintaining the concentration of borohydride species in the borane-tetrahydrofuran complex below approximately 0.005 moles per mole of $BH_3$ before reduction of the prochiral substrate with the borane-tetrahydrofuran complex.

7. The method of claim 1 wherein the borane reagent contains a borohydride, the method further comprising the step of: reducing the detrimental effect of the borohydride species on enantioselectivity by adding a Lewis acid.

8. The method of claim 7 wherein the Lewis acid is BF3, BF3 etherate complex, ZrCl4, AlCl3, FeCl3 or TiCl4.

9. The method of claim 7 wherein the Lewis acid is BF3 or BF3 etherate complex.

* * * * *